United States Patent [19]

Brown

[11] Patent Number: 4,665,905

[45] Date of Patent: May 19, 1987

[54] DYNAMIC ELBOW AND KNEE EXTENSION BRACE

[76] Inventor: Charles S. Brown, 1395 Hunn Rd., Yuba City, Calif. 95991

[21] Appl. No.: 872,148

[22] Filed: Jun. 9, 1986

[51] Int. Cl.⁴ .............................. A61F 5/10; A61F 5/04
[52] U.S. Cl. ...................... 128/80 C; 128/77; 128/87 R; 128/88; 128/84 R
[58] Field of Search ............ 128/77, 80 R, 80 C, 128/80 F, 80 F, 84 R, 87 R, 88; 135/71; 272/140

[56] References Cited

U.S. PATENT DOCUMENTS

| | | | |
|---|---|---|---|
| 2,413,053 | 12/1946 | Kolarik | 128/84 R |
| 2,413,634 | 12/1946 | Kolarik | 128/80 F |
| 3,757,807 | 9/1973 | Manzo | 135/71 |
| 3,785,372 | 1/1974 | Craig | 128/80 C |
| 3,814,419 | 6/1974 | Bjorklund et al. | 272/140 X |
| 4,361,142 | 11/1982 | Lewis et al. | 128/88 X |
| 4,372,298 | 2/1983 | Lerman | 128/88 X |
| 4,397,308 | 8/1983 | Hepburn | 128/80 F X |
| 4,419,991 | 12/1983 | Lee | 128/88 |
| 4,433,679 | 2/1984 | Mauldin et al. | 128/80 F |
| 4,440,159 | 4/1984 | Cochran | 128/88 X |
| 4,441,489 | 4/1984 | Evans et al. | 128/77 |
| 4,456,002 | 6/1984 | Barber et al. | 128/77 |

FOREIGN PATENT DOCUMENTS 0663247 12/1951 United Kingdom .................. 135/71

Primary Examiner—Robert A. Hafer
Assistant Examiner—Kathleen J. D'Arrigo

[57] ABSTRACT

A wire frame structure of two parallel aligned members are formed into a compression spring centrally positioned to provide controlled force at each end. U-shaped yokes are adjustably affixed to the aligned members, one to each end. The yokes are hinged to cuffs suitable for attachment to human arm or leg members by self-fastening straps and adjacent the center springs, two additional securing straps are provided. In use, the brace assemblage provides a dynamic tension to apply a controlled force on an elbow or knee flexion contracture.

4 Claims, 5 Drawing Figures

DYNAMIC ELBOW AND KNEE EXTENSION BRACE

BACKGROUND OF THE INVENTION

1. Field of the Invention

This invention relates to dynamic splints useful for rehabilitation and the prevention of elbow flexion contractors following injury or dysfunction.

2. Description of the Prior Art

In the issued past-art patents seen, there were no devices offered specifically for the same purpose as the present invention. Various types of splint structures were available for joint stablization and injury prevention. A patent issued to Mauldin et al. dated Feb. 1, 1983, U.S. Pat. No. 4,370,977, illustrates a spring and cable device as a knee and elbow brace. Most of the other devices were directed towards the prevention of sports injuries or for rehabilitation of sports injuries. A list of other patents illustrative of the field include U.S. Pat. Nos. 2,767,708, 3,814,419, 3,975,015, 4,190,902, 4,191,373, 4,299,210, 4,417,570.

SUMMARY OF THE INVENTION

A brief description of my invention entails a wire frame structure of two parallel aligned members turned into a compression spring located centrally therein to provide a controlled force at each end. The ends are fitted with adjustable U-shaped yokes which are hinged one to a wrist cuff and one to an upper arm fitting cuff. The frame is affixed with two self-holding arm straps and each cuff has one self-holding strap. The device is arranged to be fastened to the arm or leg with the central compression springs adjacent the elbow or knee joint axis. In use, my invention provides a dynamic tension to apply a controlled force on an elbow or knee flexion contracture.

Accordingly, it is a primary object of my invention to provide a light weight spring action structure useful for rehabilitation of elbow and knee injuries.

Another object of the invention is to provide a dynamic elbow extension brace to be worn for the prevention of elbow flexion contractures.

A still further object of the present invention is to provide a controlled spring wire tension brace adjustable according to patient requirements.

Another object of the invention is to provide an elbow and a knee brace structured openly for easy view and acces to an injured area.

Other objects and the many advantages of my invention will become better understood from a reading of the included specification in conjunction with the numbered parts on the supplied drawings.

DESCRIPTION OF THE PREFERRED EMBODIMENTS

Figure 1:
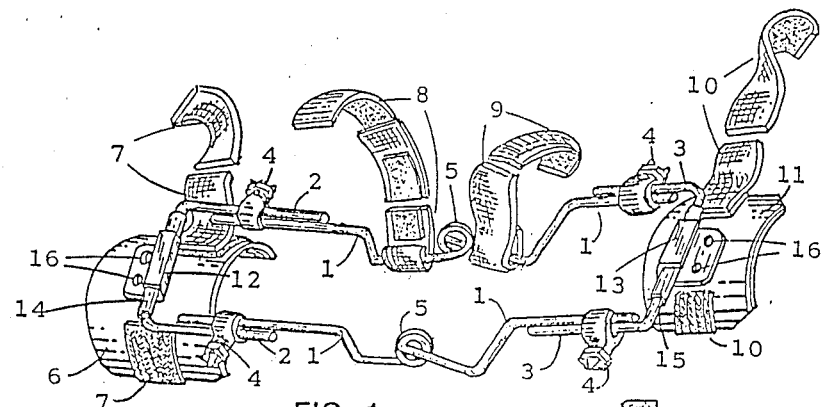
FIG. 1 is a perspective view of the present invention in an arm-use embodiment showing the relative position of the end adjustable yokes and attached cuffs and placement of the self-holding straps on either one of the longitudinal rods and on the back of the cuffs.

Referring now to the drawings at FIG. 1. Two longitudinal rods 1 in paralleling alignment are structured centrally into coil springs 5 to direct a force on a wrist cuff yoke 2 and on an arm cuff yoke 3 affixed adjustably by cuff yoke adjusters 4 at opposite ends of the structure. Wrist cuff 6 is hinged to wrist cuff yoke 2 by wrist cuff attach hinge 12 held by hinge retainer rivets 16. Wrist cuff 6 is affixed with self-holding wrist cuff strap 7. At the opposite end of the frame structure, proximal arm cuff 11 is affixed to arm cuff yoke 3 by proximal arm cuff attach hinge 13 held by hinge retainer rivets 16. Proximal arm cuff 11 is affixed with self-holding proximal arm cuff strap 10. Self-holding distal elbow strap 8 is fastened to one member of rods 1 on the wrist cuff 6 side of coil spring 5 and adjacently, on the same rod 1, self-holding proximal elbow strap 9 is fastened near coil spring 5 on the proximal arm cuff 11 side of rod 1. Wrist cuff yoke 2 and arm cuff yoke 3 can be lengthened or shortened per patient 18 requirements by loosening cuff yoke adjusters 4, moving the said yokes to required position and tightening up adjusters 4. Wrist cuff attach hinge 12 and proximal arm cuff attach hinge 13 are allowed pivotal movement as required by axle core action achieved through smooth plastic sleeves 14 and 15 encasing the yokes 2 and 3 sufficiently to pass through the wrist cuff attach hinge 12 and the proximal arm cuff attach hinge 13 to act as a bearing thereto.

Figure 2:
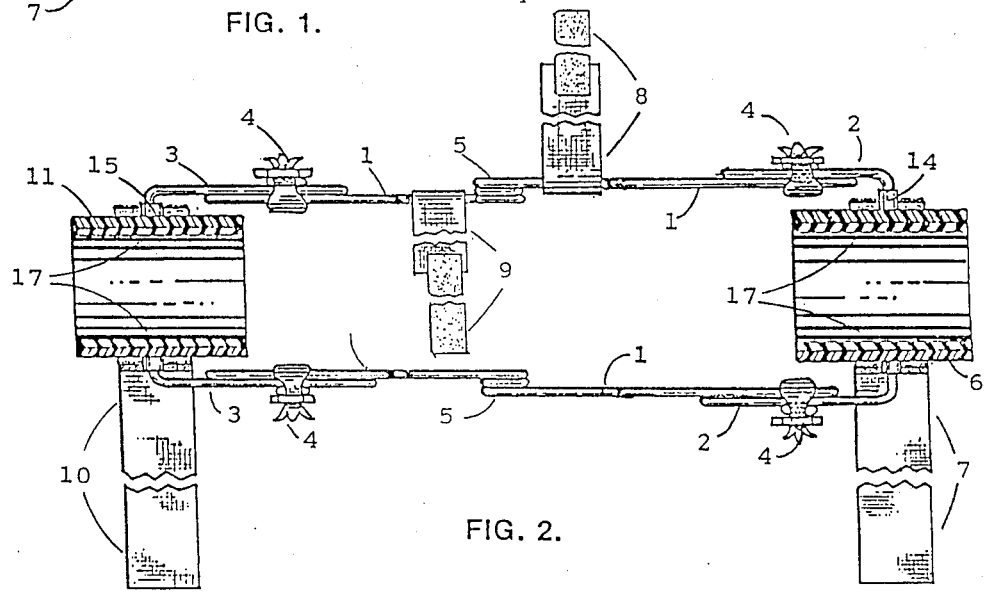
FIG. 2 shows my invention enlarged and reversed in a top plan view of an embodiment useful for leg applications illustrating the adjustable cuff-holding U-shaped yokes, the interior padded lining of the cuffs; and the elbow straps for knee use attached to the opposite longitudinal rod from the position of FIG. 1.
Figure 3:
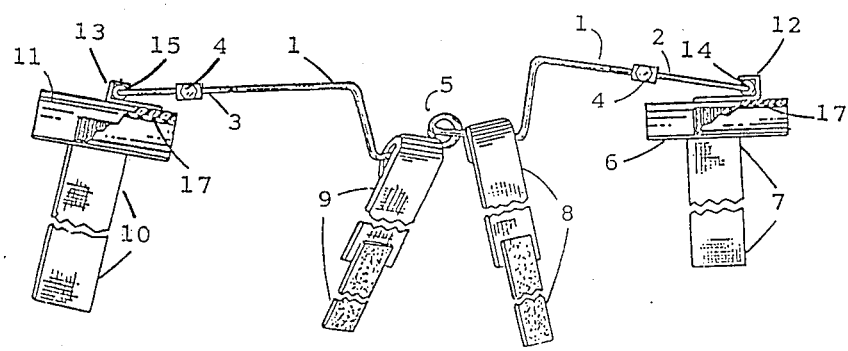
FIG. 3 is a side elevation of the invention showing the centrally positioned coil spring as a continuing part of the main frame structure as used in both the arm and leg embodiments of the invention.
Figure 4:
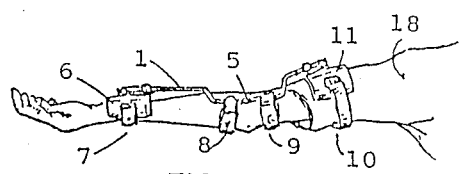
FIG. 4 illustrates my device correctly positioned on the anterior aspects of a patient's arm.
Figure 5:
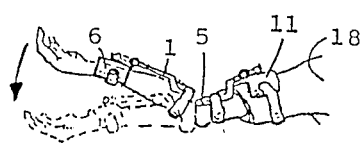
FIG. 5 shows the device in use on a patient to illustrate the intended direction of applied force.

In FIG. 2, an enlarged embodiment of the invention as illustrated is arranged for leg use at the knee joint, and for both arm and leg use, the appliances and the applications are similar. As illustrated in FIG. 2, the joint straps 8 and 9 may be affixed to either of the longitudinal rods 1 for convenience of the patient. When used for elbow rehabilitation, the dynamic elbow extension brace is strapped to anterior aspects on the arm of patient 18 as shown in FIG. 4. Force is applied by coil springs 5 to parallel rods 1. This results in a levering effect between wrist cuff 6 and coil spring 5 to apply extension force at the wrist of patient 18. The applied force is designed to extend the elbow from the illustrated bent position to the desired position indicated by dotted lines and a directional arrow in FIG. 5.

Although I have described only two embodiment of my invention in the specification, it is to be understood that other embodiments having modifications in the design and structure may be undertaken which do not depart from the scope of the appended claims.

What I claim as my invention is:

1. A dynamic elbow and knee extension brace comprising two longitudinal rods in parallel alignment structured centrally into coil springs and fastened adjustably to U-shaped yoke rods at both outer ends, each yoke rod affixed by a hinge to a wrist or lower leg cuff at one end and to a proximal arm or upper leg cuff at the other end, there being self-holding straps, one fastened to the back of each cuff and two hingedly affixed to one of the said longitudinal rods centrally adjacent the said coil spring, one on either side thereof, the said cuffs curved, padded, and malleable to conform to various human arm and leg sizes there being a plastic sleeve encompassing the yoke rod at the hinge attach position.

2. The dynamic elbow and knee extension brace of claim 1, wherein an enlarged yoke, cuff, and strap augments the said wrist yoke, cuff and strap with lower leg fitting sizes applicable to the dorsal aspects thereof.

3. The dynamic elbow and knee extension brace of claim 1, wherein an enlarged yoke, cuff, and strap augments the said proximal arm yoke, cuff, and strap with upper leg fitting sizes applicable to the dorsal aspects thereof.

4. The dynamic elbow and knee extension brace of claim 1, wherein the longitudinal rods are increased in diameter, length, and coil spring tension for leg application.

* * * * *